(12) United States Patent
Bradwell

(10) Patent No.: US 8,133,744 B1
(45) Date of Patent: Mar. 13, 2012

(54) PRODUCTION OF ANTIBODIES AND TO MEDICAL USES INVOLVING ANTIBODIES

(75) Inventor: Arthur Randell Bradwell, Birmingham (GB)

(73) Assignee: The Binding Site Group Limited, Birmingham (GB)

( * ) Notice: Subject to any disclaimer, the term of this patent is extended or adjusted under 35 U.S.C. 154(b) by 0 days.

(21) Appl. No.: 08/741,822

(22) Filed: Oct. 31, 1996

(30) Foreign Application Priority Data

Nov. 3, 1995 (GB) .................................. 9522554.6
Jul. 24, 1996 (GB) .................................. 9615578.3

(51) Int. Cl.
*G01N 33/531* (2006.01)
*G01N 33/53* (2006.01)
(52) U.S. Cl. ........................................ 436/547; 435/7.1
(58) Field of Classification Search ............... 424/130.1; 435/71.1; 436/547, 548
See application file for complete search history.

(56) References Cited

U.S. PATENT DOCUMENTS 5,585,250 A * 12/1996 Garrity et al. ................. 435/69.3

FOREIGN PATENT DOCUMENTS

| DE | 27 37 953 | | 3/1978 |
|---|---|---|---|
| EP | 0328276 | * | 1/1989 |
| GB | 1587193 | | 4/1981 |
| WO | WO-88/02594 | | 4/1988 |
| WO | WO-97/17372 | | 5/1997 |

OTHER PUBLICATIONS

Caulfield et al. J. Immunol. 138:3680-3, 1987, abstract thereof.*
Bhogal, B.S. et al., "Production of mycoplasma-specific antisera in rabbit immunologically tolerized at birth to mycoplasma medium constituents," Journal of Immunological Methods, 97 (1987) 191-199.
Dispenzieri, A. et al., "International Myeloma Working Group guidelines for serum-free light chain analysis in multiple myeloma and related disorders," Leukemia (2009) 23, 215-224.
Gertz, M.A. et al., "Definition of Organ Involvement and Treatment Response in Immunoglobulin Light Chain Amyloidosis (AL): A Consensus Opinion From the 10th International Symposium on Amyloid and Amyloidosis," American Journal of Hematology 79:319-328 (2005).
Holbrook, F.L. et al., "Tolerization as a tool for generating novel monoclonal antibodies," Immunology and Cell Biology (2002) 80, 319-322.
Katzmann, J. A. et al., "Elimination of the Need for Urine Studies in the Screening Algorithm for Monoclonal Gammopathies by Using Serum Immunofixation and Free Light Chain Assays," Mayo Clin Proc., Dec. 2006:81(12):1575-1578.
Katzmann, J.A. et al., "Screening Panels for Detection of Monoclonal Gammopathies," Clinical Chemistry 55:8 1517-1522 (2009).
Lebron, J.A. et al., "Tolerization of adult mice to immunodominant proteins before monoclonal antibody production," Journal of Immunological Methods 222 (1999)59-63.
Pulendran, B. et al., "A form of immunologic tolerance through impairment of germinal center development," Proc. Natl. Acad. Sci. USA, vol. 91, pp. 2639-2643, Mar. 1994, Immunology.
Durie, B.G.M. et al., "Assessing response rates in clinical trials of treatment for relapsed or refractory multiple myeloma: a study of bortezomib and thalidomide by H Prince, Brad Schenkel and Linda Mileshkin," Letter to the Editor, *Leukemia* advance online publication, Feb. 15, 2007, vol. 1.
Berek, C. "Antibodies specific for different T15 idiotopes induce neonatal suppression of the T15 idiotype," Eur. J. Immunology, vol. 13, Issue 9, pp. 766-772, 1983.
Strayer, D.S. et al., "Neonatal Tolerance Induced by Antibody against Antibody against Antigen-Specific Receptor," Science, vol. 186, Feb. 20, 1974, pp. 640-643.

* cited by examiner

*Primary Examiner* — Ronald Schwadron
(74) *Attorney, Agent, or Firm* — Wilmer Cutler Pickering Hale and Dorr LLP

(57) ABSTRACT

A method of making antibodies to a selected part P of an immunoglobulin molecule ZP, Z comprising the non-selected part of ZP, P being the selected part of ZP which comprises a hidden epitope of the light chain, said method comprises tolerizing the source of antibodies, by administering to the source a compound containing the non-selected part Z or a part of Z and administering antibodies to the non-selected part Z or a part of Z; wherein these administered antibodies are specific to an Fc region of ZP;

and immunizing the source of antibodies with part of ZP having the selected part P exposed; and wherein Z comprises non-hidden epitopes of said immunoglobulin molecule, and wherein said compound containing the non-selected part of said molecule comprises a whole immunoglobulin, and wherein immunizing the source of antibodies with part of ZP comprises immunizing with free light chain.

31 Claims, 6 Drawing Sheets

B-cell Stimulation

B-cell Inhibition

B-cell Inhibition

B-cells that recognize common epitope inhibited

Whole immunoglobulin

Free light chains

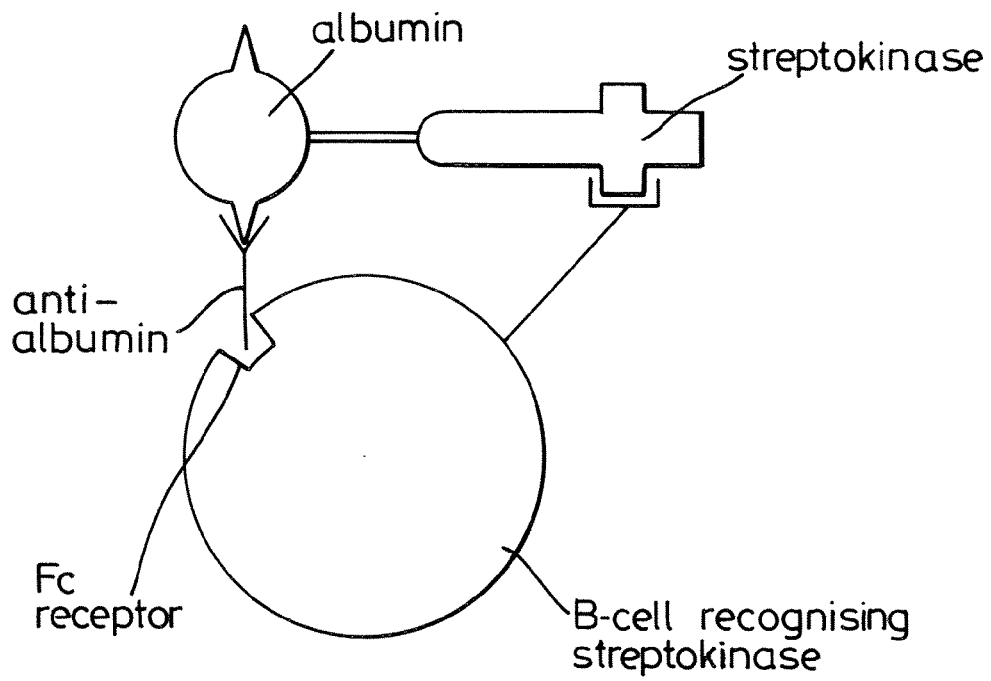
Fig. 16  B-cell switched off
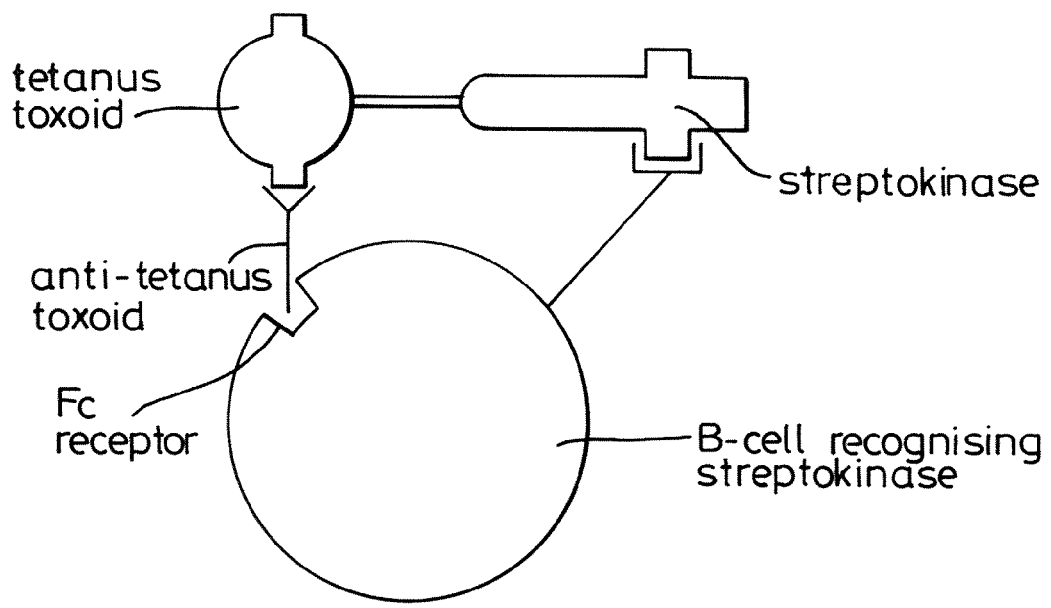
Fig. 17  B-cell switched off

PRODUCTION OF ANTIBODIES AND TO MEDICAL USES INVOLVING ANTIBODIES

This invention relates to the production of antibodies that are specific, and to medical applications involving administering antibodies and involving taking advantage of the specificity of the antibody-B cell interaction.

PRIOR ART

The fact that administering antibodies to a living animal can tolerise the animal to the antigen corresponding to the administered antibodies has been known for very many years indeed. Treatment of pregnant women who have rhesus positive babies with antibodies to rhesus D is long established.

THE INVENTION IN BROAD TERMS

The present invention resides in part in the appreciation that the theory that it is possible to switch off an immune response from naive B cells by administering antibodies to give a negative signal at their $F_c$ receptors is not just an immunological curiosity, but can be used for substantial beneficial technical effect and has wide industrial application when it is desired to switch off an immunological response to a single antigen (or a narrow group of antigens) and yet maintain a good immunological response to other antigens. Part of the invention also resides in realising that such circumstances exist and that there is a need for such a thing.

This patent application will discuss three aspects of the invention:
1) the concept of producing antibodies specific to a particular antigenic substance (which could be part of a molecule/one or more epitopes of a molecule, or could be one antigen (or a few antigens) from a cocktail of antigens).
ii) a) the realisation that once it is possible to produce such highly specific antibodies it is desirable in some circumstances to switch off the immune system of a patient specifically to a particular antigenic substance and yet not switch it off generally, allowing as to administer deliberately in a medicament (usually by injection) both an antigen (with desirable physiological activity) and also antibodies to said antigen (to suppress immune system attack on the antigen);
b) there is then the realisation that administration of "switching off" antibodies to a patient with a deliberately introduced physiologically active substance is new in itself without the antibodies necessarily being produced to be so specific as those of the first aspect of the invention; and
iii) the further realisation that once we know how to switch off the immune system to an externally administered useful substance by also administering antibodies to that substance we can achieve the same overall effect by relying on the already existing population of antibodies in a patient to switch off B cells to the foreign substance if we associate (conjugate) the administered foreign substance with another antigen specific to an antibody from the pre-existing antibody population in the patient (eg most people have anti-tetanus toxoid antibodies already in their blood, from earlier tetanus toxoid immunisation, and we can conjugate the desired physiologically active substance with, for example, tetanus toxoid, and therefore depress the immune reaction to the desired substance). We may also administer non-conjugated desired substance as well.

All of the above aspects of the invention rely upon the realisation of how to exploit technologically the antibody/antigen/naive B cell relationship, and the role of naive B cells in antibody production.

Producing Specific Antibodies

One aspect of this invention relates to the production of specific antibodies. One use for specific antibodies is test kits incorporating them.

Antibodies for test kits to look for an antigen can be produced by injecting an animal with the antigen in question, allowing its immunological response to produce antibodies to it, and then extracting the antibodies and incorporating them in a kit. This is known prior art.

If it is desired to produce an antibody to a protein that is only slightly different from another protein, for which no antibody response is required, this can be difficult to achieve. It can be impossible if the difference is very small.

According to a first aspect the invention comprises a method of making antibodies to a selected part of a molecule comprising tolerising the immunological system of an antibody source to a part of said molecule that is not the selected part (non-selected part), and immunising the antibody source with said selected part of the molecule, allowing the antibody source to produce antibodies specific to said selected part of the molecule, and extracting the antibodies produced from the antibody source.

Tolerising is preferably achieved by introducing antibodies to the non-selected part to the antibody source.

This is found to produce more antibodies that are specific to the selected part and do not have a response to the non-selected part.

The selected part of the molecule may be the difference between two similar molecules (e.g. allotypes), or it may be a portion only of a single molecule. Thus the non-selected part of a molecule may in fact comprise a different similar molecule (e.g. a first protein may have one or more epitopes that are different from a second molecule, and the second molecule may be the "non-selected part" for tolerisation, and the different epitopes may be the selected part to which specific antibodies are to be raised).

Preferably the antibody source is an animal. It may be possible to produce antibodies in vitro, but it is preferred to use an animal (preferably non-human).

Preferably the antibody source is tolerised with all, or substantially all, of said molecule that is not said selected part. This may be achieved by tolerising with an incomplete portion of a molecule, or by tolerising with a similar molecule that has the non-selected part, but not the selected part (e.g. an allotype if the selected part is the difference between two allotypes). The antibody source may be immunised with the selected part of the molecule by injecting the whole, or substantially the whole, molecule into it. Alternatively substantially only the selected part may be immunised.

Preferably one method comprises tolerising the immunological system of the antibody source to the non-selected part of the molecule by immunising an antibody source with the non-selected part antigen to raise an antibody to the non-selected part, extracting the antibody to the non-selected part and using the antibody to the non-selected part to tolerise the antibody source to enhance the production of antibodies to the selected part.

It will be appreciated that tolerising the immunological antibodies to a non-selected part of a first molecule may be achieved by introducing antibodies to the non-selected fragment of the first molecule in question, or by introducing antibodies to another molecule, a second molecule, that has the non-selected part of the first molecule in question plus another part or parts (but not the selected part of the first molecule).

This effectively augments the production of antibodies of the system to the difference between the two molecules (or between the tolerised fragment of molecule and the selected part). This can help produce a good production of antibodies to one allotype, but not another.

The antibody source that is used to produce the antibody to the non-selected part is preferably not the same source (animal) that is later used to produce the antibody to the selected part. That is to say a different source (animal of the same species) has the antibody to the non-selected part used to tolerise it for the production of antibody to the selected part.

The animal, or other antibody source, chosen to produce the antibody to the selected part should preferably not have been immunised to the non-selected part beforehand. This is because once an immunological response has been established in a particular animal it will have memory B cells which cannot be switched off by introducing antibodies to the protein in question (non-selected part) and so the animal when immunised with the selected part (as part of the protein used to immunise) will produce antibodies to both the selected part and the non-selected part. The yield of antibodies to the selected part will be less, and there will be two different antibodies which will need to be separated. This is all best avoided by ensuring that the animal to which the selected part immunising injection is given has not already been immunised to the non-selected part (and clearly this includes the entire protein which would contain the selected and non-selected parts).

The antibody to the selected part and/or non-selected part may be extracted from the animal in its blood or from some other substance or material produced by the animal. We may extract about a pint of blood from an animal such as a sheep.

Preferably the antibody to the non-selected part is purified before being introduced to the animal that is to produce the antibody to the selected part. The purification is preferably an affinity purification. If there is a wider mix of antibodies in the extract from the animal purification is more difficult. By preferentially producing antibodies of substantially only one kind the difficulty of the purification stage is reduced.

The animal (or other antibody source) that is to produce the antibody to the desired part may be tolerised to the non-selected protein part (or antibodies to that part) at the same time as it is immunised with the selected part, or beforehand, or afterwards. Any time within a day or so either side of immunisation is seen as being a suitable time for tolerisation.

It will be appreciated that the present invention allows the production of polyclonal antibodies faster, and to only a part of a naturally occurring molecule, and enables a greater concentration in the animal extract of antibodies of the desired kind to be obtained.

The same invention can be used to stimulate the antibody response to one desired antigen from, for example, an impure antigen injection (where there are other antigens as well as the desired one).

According to a second aspect of the invention we provide a method of making antibodies to a selected antigen (first antigen) selected from a plurality of antigens (other antigens) to which an antibody source is exposed, the method comprising tolerising the immunological system of the antibody source to said other antigens, and not to said first antigen; and immunising the antibody source with said first antigen, allowing the antibody source to produce antibodies to said first antigen; and extracting the antibodies produced from the antibody source.

We have also found that if the antibody source has administered to it an antigen comprising the non-selected epitope (s), or "other" antigens as the case may be, before antibodies to the non-selected epitopes (s), or "other" antigens, are administered (and the selected or first antigen) we get even better production of the antibodies to the selected epitope, or to the first antigen, as the case may be. We may administer the antigen (non-selected epitopes (s)), or "other" antigens at least 1 or 2 days and preferably 3 days, before tolerising with the unwanted antibodies.

According to a third aspect the invention comprises providing a test kit having a preparation that contains antibodies to a selected part, or epitope, of a protein, the antibodies having been made in accordance with the first aspect of the invention.

Preferably the test kit is an immunological test kit.

The antibodies may be linked to an adjuvant, or to a particle or microsphere, such as a polystyrene microsphere.

Hitherto kits which were specific to part only of a protein have been difficult to make, and produce results which are not satisfactory. Preferably the protein is naturally occurring, most preferably in man.

The kit may contain instructions on how to use it. It may contain a bottle of control material, and/or a bottle of reference standard material in addition to the bottle of antibody material. The containers of antibodies, control material, and standard reference material will, if provided, usually be labelled as such. It is envisaged that the antibodies in the kit would be provided in a preparation that has between 1-5 mg/l of antibodies.

The kit is preferably suitable to be used on automated test apparatus (of course the kit could be used manually, but it is preferably sensitive enough to allow the test to be run on existing automated laboratory systems).

When treating a patient (or considering beginning treatment) a diagnostic test may be performed before a decision is made.

The skilled practitioner in the field of antibody production, possibly in consultation with an expert in splitting molecules at a desired place, or binding molecules to a particular region, should be able to produce an antigen with the active part masked, or removed, without any undue difficulty. Some trial and error may be required to find the best excision point, or the best way of masking the active region, but no further invention will be required.

In the case where we tolerise to the whole of a substance the skilled man has no difficulty in producing, and purifying, antibodies (e.g. sheep or human, or other mammal) to a substance.

According to another aspect, the invention comprises a method of producing antibodies to a hidden part, part P, of a molecule Z, comprising tolerising to the molecule Z, or a part of molecule Z that has the part of molecule Z that hides the hidden part P; and immunising with the molecule Z, or part of molecule Z, which has its hidden part P exposed.

An example of the invention will be described by way of example only later, but first we shall discuss the other wide aspects of the invention.

Specific Switching Off of a Patients Immune Response to Specific Antigens for Beneficial Effect This aspect of the invention relates to the treatment of disorders which require the administration to a patient (human or animal) a substance (synthetically produced or naturally produced) which elicits an immune response in the patient, and to medicaments for use in such treatments, and to kits for use in such treatment.

Many treatments require the injection (or other administration) of a substance to a patient so that the substance will have a beneficial physiological effect. Sometimes, and in some patients, (and not necessarily all patients) the efficacy of a second treatment, or a further treatment, beyond a certain point with the substance is reduced by the immune system of the patient producing antibodies to the substance administered. The physiological working of the substance can be severely impaired, even to the point where there is so little beneficial effect it is not worth administering the substance to the patient. Greater and greater doses of the substance can be given to try to fight the immune system of the patient, but the problem of attack on the physiologically active substance remains. In the end the immune system produces enough antibodies to nullify (effectively) the higher dose, and the cycle begins again. Examples of such problems are the treatment of muscle spasms in the neck or face muscles with intramuscular injections of Botulinus Toxin, and the treatment of multiple sclerosis with interferon.

Unfortunately, that is not the only problem. The immune system of a patient can react so strongly to a second dose of a substance, or further dose beyond a certain point, that the patient may experience anaphylactic shock. Administering a further dose of the substance at all, let alone at a higher dosage, may risk the patient's life.

When Botulinus Toxin is used to treat muscle spasm (e.g. blepharospasm and hemifacial spasm) some patients never produce a reaction to repeated doses, but some find that the beneficial effect of an injection of Botulinus Toxin is diminished after a few injections (or even one). Perhaps 10 or 15% of patients eventually become unresponsive. We believe that this is because of their immune system creating antibodies to the antigen that is injected, and attacking it (perhaps complexing/cross-linking it so as to facilitate its removal from the blood stream, or binding to it so as to destroy/impair its physiological activity).

Hitherto the problems of patients becoming unresponsive to Botulinus Toxin injections has been overcome by developing a new strain of Botulinus that produces chemicals that have a similar physiological effect to those of the first strain but that are seen as a different antigen to those of the first strain by the Immune System.

Developing new strains of Botulinus costs millions of pounds.

Interferons are used to treat multiple sclerosis. Again, some patients experience a reaction to further injections of Interferons, and we believe that their immune system produces antibodies to the interferon to combat it, and reduce or eliminate its physiological effect. The antibodies may attach to the interferon molecules, cross-linking them, making it easier for the body to excrete the complexes from the blood, removing the interferon from effective presence near the sites where it is needed (this possible mechanism may also apply to the removal of other physiologically active substances from the patient's body). Giving more and more interferon works for a while, but is expensive.

A further example of this kind of problem is the case of streptokinase administered for myocardial infarction. Antibodies prevent a second dose from being given usefully because of the immune response of a patient. At present this problem is overcome by genetically engineering a similar product which has a similar effect physiologically, but which is seen as a "new" substance to the Immune System, rather than a "known" antigen for which the Immune System has memory cells ready to pour out antibodies against the antigen in huge numbers. The use of a similar, but different, substance does work, but the synthetic alternative to streptokinase costs 10 times as much. Furthermore, a third alternative substance may be needed should a third administration be required, in the future.

Another example is TNF administered to relieve arthritis. This has been shown to work wonderfully for some patients for one or two administrations, and then the Immune System reacts to the "foreign" material so as to render subsequent treatments ineffective. Currently some patients treated with TNF have a few months of relief and then go back to experiencing the effects of arthritis.

According to a first aspect of the invention we provide a medicament for use in treating a disorder that requires the administration of a substance which elicits an immune response from a patient, the medicament comprising;

said substance (which has in use a physiological effect on the patient);

and antibodies to at least a first part of (and preferably the whole of, or substantially the whole of) said substance;

said first part of said substance being such that but for said antibodies to it present in the medicament it could, in use, elicit a significant immune response in the patient to whom it is to be administered;

and in which the antibodies to the first part of the substance do not prevent the substance from having its desired physiological effect.

This has the effect of switching off the immune system of the patient to the antigen that we want to administer, preventing the development of a strong immune response to further administrations of the substance.

We can therefore administer the substance again, without a strong immunological response. If we administer it within a few months of the tolerisation of the patient to the first part of the substance there may be no need to re-administer the antibodies to the first part when administering the further dose of substance.

If too long a time has passed we may prefer again to administer the antibodies with the substance for a second or subsequent dose.

Preferably we administer antibodies to substantially the whole of said substance. This can mean that substantially no part of the substance elicits an immune response (or at least not a strong response).

It is "known" in the prior art that administering antibodies to a physiologically/pharmacologically active substance renders that substance less efficient in the body, and is therefore undesirable. We have appreciated that this natural prejudice against administering antibodies to the very external substance that is being administered for a beneficial reason is wrong. If antibodies are given at a low enough dose they can be beneficial.

A low enough dose is that which produces the desired effect and can, for any active substance, be determined experimentally without further inventive activity: it merely requires tests. The preferred dosage of antibodies may vary with the antigen dose and antigen size as well as with the size of the person/animal being treated.

By way of possible guidance a suitable dose of antibodies for an adult human might be in the microgramme range (eg about 25 μg, or above), but it will depend upon the substance and the patient.

We appreciate that a method of treatment of the human or animal body is not patentable per se in the UK, and in some European countries, but it is patentable in other overseas countries. We seek in such countries definitions of the invention in ways that are patentable in the UK, and under the EPC (for example a medicament per se, a kit per se, a second medical indication "Swiss" definition; and as ways of achieving a technical effect, such as reducing the volume of drug needed, or making a cheaper medicament).

We may prefer to ensure that the antibodies that are administered have no high affinity antibodies to a second part of the substance (or indeed substantially no antibodies to a second part of the substance. Said second part may be a part that is associated, in use, with the physiological effect on the body).

According to another aspect the invention comprises the use of antibodies to a physiologically active molecule in the production of a medicament having said molecule in it for the treatment of a disease or disorder susceptible to treatment by said molecule.

The antibodies are preferably used at low level such as not to effect, substantially, the physiological activity of the molecule. The antibodies to the molecule used in the production of the medicament are preferably of high affinity.

According to another aspect of the invention we provide a kit for use in treating a disorder that is alleviated by the administration of a substance, the kit comprising said substance and antibodies; the antibodies being antibodies to at least a part of said substance.

The antibodies are preferably provided in a kit in a predetermined dosage. The antibodies may be provided in a syringe or injector, or in a cartridge or ampoule for a syringe or injector. The kit may have instructions on how to use the antibodies. The containers holding the antibodies and/or substance are preferably provided with identification means (e.g. a label) indicating their identity and/or purpose.

The substance, or the antibodies, or both, may be provided with a pharmacologically acceptable carrier.

The substance and the antibodies may be provided in the same medium, or are adapted to be injected sequentially or simultaneously.

According to a further aspect of the invention we provide a method of preventing an unwanted immune response to an antigen, whilst allowing the antigen to be physiologically active, the method comprising tolerising a patient (human or animal) to substantially all parts of or at least one or some parts of the antigen without destroying the physiological effect of the antigen.

Another aspect of the invention comprises the use of antibodies specific to a physiologically active substance in order to improve the efficacy of treating a patient with the substance.

Another aspect of the invention comprises the use of antibodies to a physiologically active substance in order to avoid the need to increase substantially the dosage of the substance necessary in repeated administration of the substance to achieve a desired physiological effect in a patient.

Another aspect of the invention comprises the use of antibodies to a physiologically active substance in order to increase the number of doses, over time, that can be given to a patient before the efficacy of the dose of the substance is reduced by the immune response of the patient.

According to a further aspect of the invention we provide a method of treating a disease or disorder comprising administering a physiologically active substance that has a beneficial physiological effect to alleviate or ameliorate the disease or disorder (or a symptom), and also tolerising the immune system of the patient to at least a part of the substance (and preferably to substantially all parts of the substance), the part of the substance being a part that would otherwise produce a significant immune response and generate antibodies to the part if it were not for the tolerising of the immune system, the tolerising of the immune system being achieved by administering, at a suitable dosage, antibodies to said substance.

Preferably the method further comprises administering antibodies to the first part, but not to a second part, of the substance to the patient to tolerise their immune system in which the antibodies may be administered at the same time as the substance, or sooner or later than administering the substance, but at a time close enough to the administration of the substance to suppress the response of the immune system to the part of the antigen to which the antibodies are active (e.g. within about a day before or after, or within 2 days). The antibodies to the substance are administered to the patient in the same injection, or at the same time, as is the physiologically active substance.

According to another aspect the invention comprises the use of a higher than normally found in the human body concentration of antibodies (or purer than normally found in the human body antibodies) to a chosen epitope of a substance, substance Y, in the preparation of a medicament for use in the treatment of a disease, the disease preferably having a substance, substance Y, associated with it, or with its treatment.

We may provide a package of antibodies in a pharmacologically acceptable carrier, there being antibodies to at least a portion of a physiologically active chemical or substance, the antibodies to the portion, in use, being such that they do not completely destroy the physiological activity of the substance.

The package may also have antibodies to a second or third, different, portion of the substance, and these antibodies also do not destroy the physiological activity of the substance. There may be antibodies to a fourth different, or fourth and fifth different, or a fourth, fifth and sixth different, or a fourth, fifth, sixth, and seventh different, or a fourth, fifth, sixth, seventh, and further different portions of the substance, and in which the antibodies do not in use render the substance physiologically inactive. There may be substantial immunological response (or any immunological response) beyond the antibodies to the first, and if present second, third and subsequent regions of the substance. There may be no (or substantially no) proteinatious matter other than the antibodies to the first, and if present second, third and subsequent regions.

The substance may be any of:
streptokinase; or
TNF; or
a selection; or
a cytokine; or
an antibody of a different species (e.g. a tumour targeting antibody, or a Fab antibody) or
an erythropoetin; or
Factor VIII; or
an antisera (e.g. botulism or diptheria antisera); or
an antitoxin (e.g. antitoxin to snake bite venom); or
interferon; or
Botulinus toxin.

This aspect of the invention will now be described in more detail later, but first we shall discuss the third broad area of the invention.

Suppressing Immune Response to Foreign Substances by Associating the Substance with an Antigen and Ensuring that Antibodies to that Antigen are Present A third broad aspect of the invention is concerned with the use of the same ideas previously discussed, our realisation that switching off B-cells by triggering their Fc receptors with antibodies to the antigen we want to introduce deliberately. We have further realised that the antibody that switches off the B-cell does not have to be the antibody to the same antigen as delivers the beneficial physiological effect ("the substance"). If we can get B cells that recognise the substance to be switched off by any antibodies the substance can avoid attack by the immune system. Accordingly, we propose to bind the active substance to a second antigen and ensure that antibodies to the second antigen are present at levels such as to switch off the B-cells that recognise the substance.

According to a further aspect of the invention we provide a method of avoiding or reducing immune system recognition of a physiologically active substance by binding said substance to a second, different, antigen and ensuring that there are antibodies to said second substance present in the body of the patient at a level so as to suppress the operation of naive B cells which would otherwise recognise said substance.

We may also administer unconjugated active substances. So long as the B-cells that recognise the substance are switched off unconjugated physiologically active substance does not trigger them significantly. Thus even if conjugating the physiologically active substance with the second antigen impairs the physiological activity of the substance (which it might do in some circumstances) we can still deliver physiologically active substance.

It will be appreciated that the conjugation of the substance must still leave a binding site free to enable it to be bound to the B-cell that recognises that binding site, and that the conjugation of the second antigen must still leave it with an active binding site so that antibodies to it can bind.

The antibodies to the second antigen may be administered to the patient. Alternatively, or additionally, the patient may have a pre-existing population of antibodies to the second antigen in their body. Thus we may avoid the need to administer antibodies.

We may select the second antigen to be one to which many people already have antibodies (e.g. tetanus toxoid).

We may perform a screening test to screen a patient to ensure that they do have a pre-existing population of suitable antibodies.

According to another aspect of the invention we provide a medicament for use in the treatment of a disorder which can be alleviated by the administration of a substance, the medicament having said substance (a first antigen), but said substance being conjugated with a second antigen.

The second antigen may be tetanus toxoid. The second antigen may be an antigen to which the patient, in use, has pre-existing antibodies. The second antigen may be an antigen to which at least a threshold proportion of the human population of the country to which the this patent derived from this application relates has antibodies present in them to a level such as to switch off substantially B-cells which recognise the substance when the conjugate is administered, said threshold proportion comprising at least 20%, or 30%, or 40%, or 50%, or 60%, or 70%, or 80%, or 90% of the human population over the age of two years.

As will be appreciated, the above definition depends upon the characteristics of the human population of the country in question, but then so will the efficacy of the treatment. It is perfectly possible to know, for any country, whether a second antigen in question falls within the ranges defined.

The medicament may also have antibodies to the second antigen. These will be at levels so as to achieve the desired result.

The medicament will usually have a pharmacallogically acceptable carrier for the conjugate and/or antibodies to the second antigen.

The medicament may be substantially free, or totally free, of any other immunogenic antigens and/or other physiologically active substances (beyond the one to give the desired physiological effect).

According to another aspect of the invention comprises the use of a conjugate of physiologically active substance (first antigen) with a second antigen in the preparation of a medicament for the treatment of a disease or a disorder which administration of the physiologically active substance will alleviate.

Preferably the use further comprises selecting the second antigen to be one that the patient to whom the medicament will be administered already has antibodies to the second antigen.

We may use both the conjugate and free, unconjugated, physiologically active substance in the preparation of the medicament.

The medicament may comprise a single liquid adapted to be injected into a patient. The medicament may comprise two liquids adapted to be injected into a patient, possibly separated, possibly from a multi-compartment injector.

According to another aspect of the invention we provide a kit comprising:

a conjugate of a physiologically active substance (first antigen) and a second, different, antigen.

Preferably the kit has one or more of the following:— i) a pharmacallogically acceptable carrier;

ii) antibodies to the second antigen (either in the same carrier medium as the conjugate or in a separate carrier medium, the medium or media, preferably being provided in containers);

iii) an injector;

iv) instructions on how to use the kit;

v) a test kit adapted to test a patient to ascertain whether they have a pre-existing population of antibodies to the second antigen;

vi) a plurality of containers having respective, different conjugates in them, the conjugates differing in their second antigen;

vii) a screening test adapted to identify the presence of a plurality of antibodies corresponding to the second antigens of the conjugates of vi) above.

In another aspect the invention comprises the use of a screening test (usually on a blood sample) prior to administering a conjugate of physiologically active substance (first antigen) and second antigen, the screening test looking for the presence of antibodies to the second antigen.

Possible Theory to Explain the Invention

We believe that it will be helpful to discuss a possible theory relating to the mechanism operating in the immune system which may help to explain the invention. We should, however, make it clear that this is only a theory: the invention works and we want protection for the features of the invention we have disclosed. Even if in the end a different mechanism operates we still have disclosed to the world practical steps to enable the technical effects of the invention to be obtained and are entitled to patent protection for that.

BRIEF DESCRIPTION OF THE DRAWINGS

We will illustrate the theory in relation to some examples discussed with reference to the accompanying drawings of which:—

FIG. 1 schematically illustrates a naive B-cell being stimulated by an antigen;

FIG. 2 schematically shows a different naive B-cell being inhibited from producing anti-IgG2 antibodies by the presence of antibodies to a common epitope FIG. 3 shows a naive B-cell being inhibited from producing anti-IgG1 antibodies by the presence of antibodies to a common epitope;

FIG. 16 is a schematic representation of a B cell that recognizes streptokinase being switched off by an anti-albumin antibody binding to its Fc receptor and generating a negative signal, the anti-albumin antibody being encouraged to be in the vicinity of the Fc receptor by the streptokinase being conjugated with albumin; and FIG. 17 is a schematic representation of the same sort of mechanism as shown in FIG. 16, but with anti-tetanus antibodies, already present in a patients blood, triggering the Fc receptor and tetanus toxoid being the antigen conjugated with the streptokinase.

EXAMPLE 1

Producing Specific Antibodies to IgG1

1. Every molecule of IgG1 (G1) has G1 specific epitopes as well as epitopes that are common to all the others subclasses. If we immunise solely with G1 (plus adjuvant) then the antibodies produced will react to both the G1 specific epitopes plus the common epitopes.
2. If we inject intravenously with a preparation of pure G2, G3 and G4 (in the absence of adjuvant) before the time of immunisation, we get a tolerisation effect whereby the generation of antibodies to the common epitopes is partially inhibited.
3. We have subsequently found that intravenous administration of antibodies to G2, G3 and G4 alone at the time of immunisation also reduces the immune response to the common epitopes.
4. If 2. and 3. above are combined, i.e. giving pure G2, G3 and G4 three days before immunisation, and giving antibodies to G2, G3 and G4 at the time of immunisation, then the inhibition of the immune response to the common epitopes is strongly enhanced, and only antibodies to the G1 specific epitopes are produced.

Figure 1:
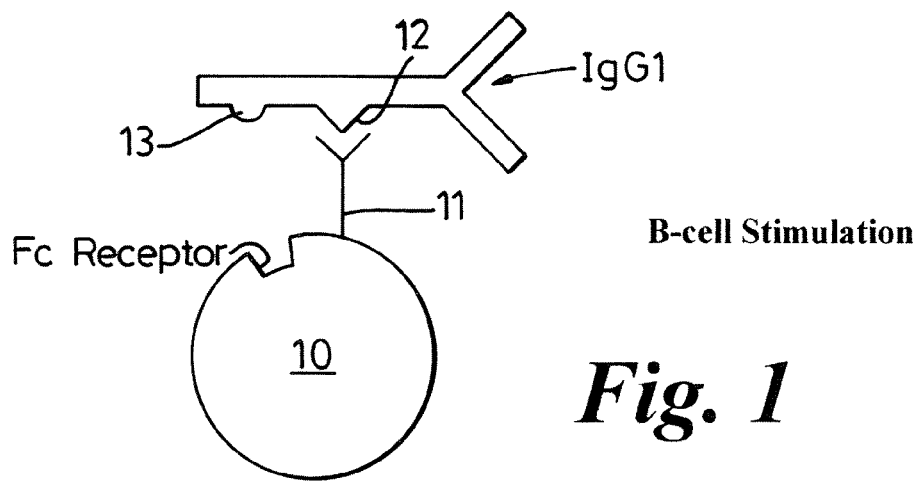

Typically, as shown in FIG. 1, a resting B-cell 10 with an antigen receptor 11 recognising a specific G1 epitope 12 will bind to G1, and will be stimulated to produce antibodies to the specific G1 epitope. Similarly, resting B-cells with an antigen receptor to a common epitope 13 on G1 will be stimulated to produce antibodies to the common epitope (which therefore will cross-react with G2 and/or G3 and/or G4).

Figure 2:
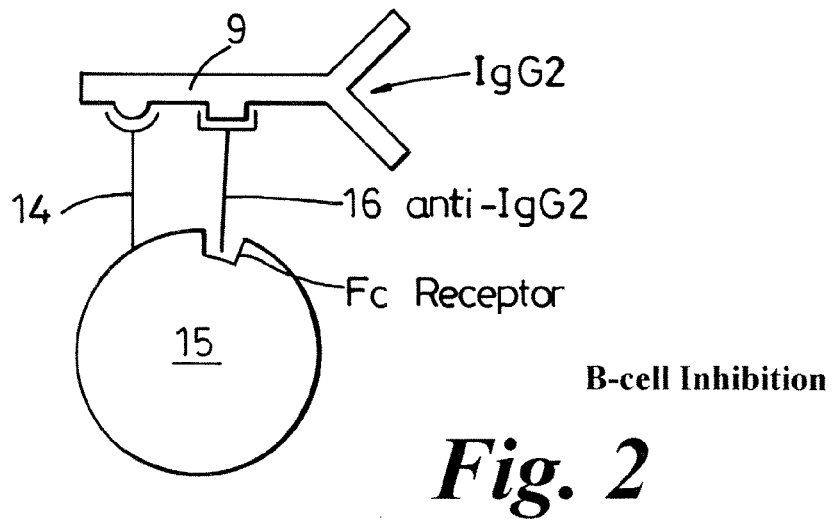

We can use the administration of specific antibodies to the other subclasses to decrease or inhibit the response to common epitopes on the target antigen (in this case G1). The mechanism of this is shown in FIG. 2. When G2 is administered (as a tolerogen 9) this is bound by the antigen receptor 14 of any B-cells 15 present that recognise the common epitope. This would normally stimulate the B-cell to produce antibodies to the common epitope. In this case however, subsequent administration of antibodies 16 specific to G2 leads to inhibition of antibody production of the B-cell. The mechanism by which this is thought to be mediated is through the binding of antibody to the G2 tolerogen, and the interaction of the antibody and the B-cell receptor (see FIG. 2). In this way, all naive B-cells recognising common epitope are inhibited, so that if G1 is given at the same time as the specific anti-G2, only B-cells recognising specific G1 epitopes are available to be stimulated. Thus only antibodies specific for G1 (and not to common epitope) are produced.

We prefer to have the tolerogen dose much greater than the immunogen dose, therefore B-cells recognising common epitopes will be "eliminated".

The tolerogens do not themselves elicit an immune response as they are administered intravenously and in the absence of adjuvant.

Figure 3:
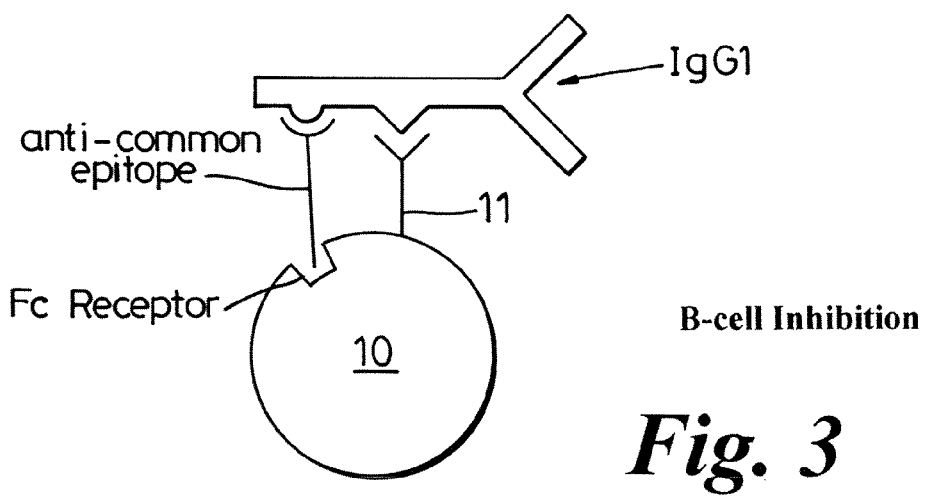

A relevant aspect of this process is that pure antibodies to G2, G3 and G4 are required; if these antibodies are impure (i.e. would also react with the common epitopes), then naive B cells recognising G1 would also be turned off as in FIG. 3. This has been demonstrated experimentally by immunising sheep (previously tolerised with pure G2, G3 and G4) with IgG1 and at the same time administering antibodies to the common epitopes. A poor response to G1 was obtained.

EXAMPLE 2

Producing Specific Antibodies to Free Lambda

Figure 4:
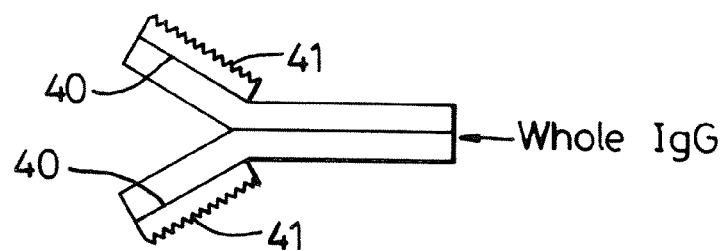
FIG. 4 shows schematically a whole IgG and a free lambda.
Figure 4:
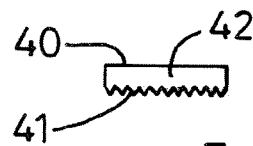

The requirement here is to make antibodies to the "hidden" epitopes 40 (which are only exposed when lambda is in the free form) and not the "exposed" epitopes 41 that are always present (on the "free" and "bound" forms of lambda). In this case the epitopes are on the same molecule, but on different sides (see FIG. 4).

Figure 5:
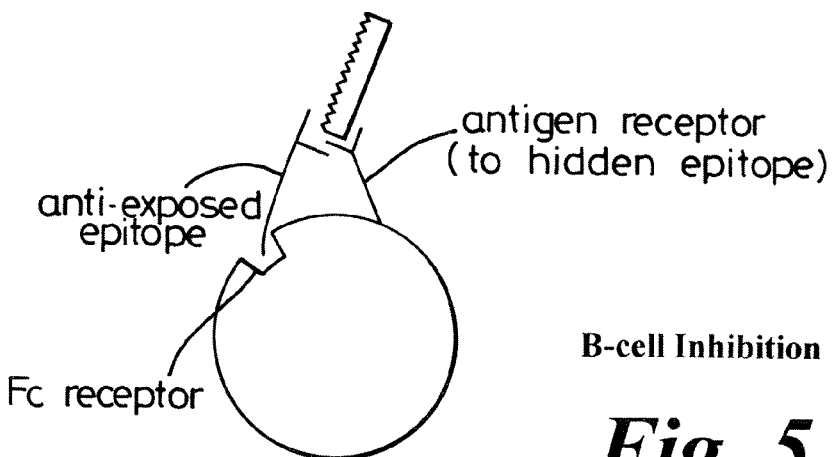
FIG. 5 shows B-cell inhibition preventing antibodies to free lambda being formed by the delivery of a negative signal to the $F_c$ receptor by an anti-exposed determinant antibody binding to the free lambda, and to the $F_c$ receptor.

Here an approach could be to raise antibodies to the exposed determinants 41, then administer these when immunising with free lambda 42. The presence of antibodies to the exposed determinants should inhibit production of antibodies to exposed determinants, allowing only antibodies to the hidden determinants to be produced. However, due to the positioning of the epitopes, some inhibition of the response to the hidden epitopes can also occur (see FIG. 5).

Figure 6:
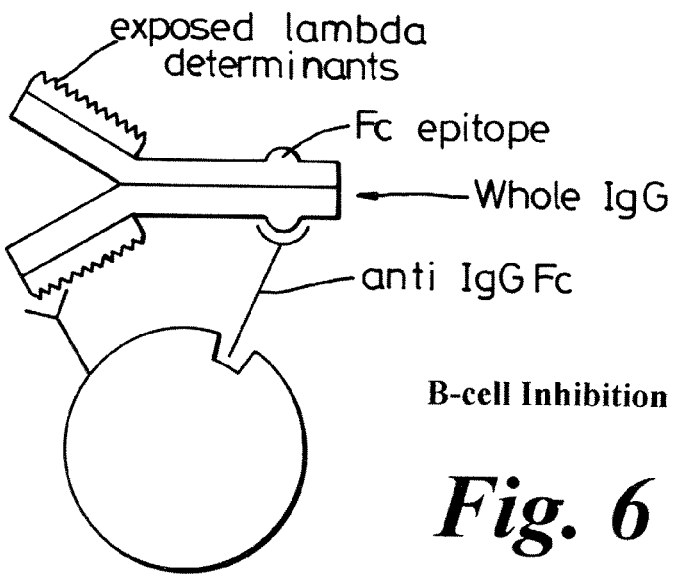
FIG. 6 shows B-cell inhibition to the production of exposed determinant antibodies by the presence of anti-exposed determined antibodies, ensuring that B-cells for such production are not stimulated, whereas B-cells for hidden determinants may still be stimulated.
Figure 7:
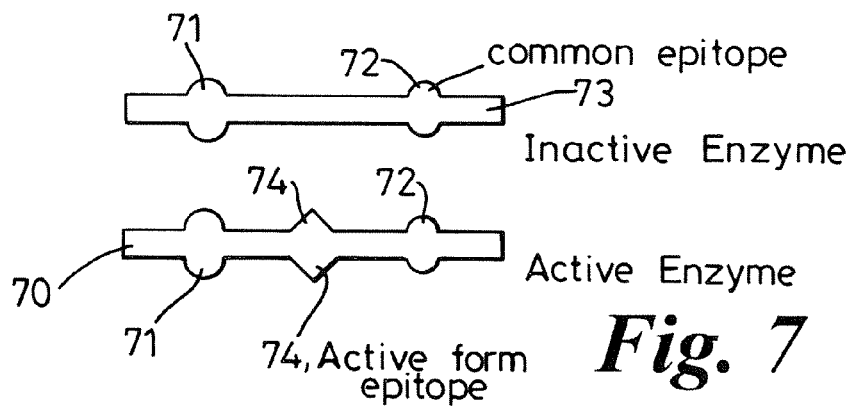
FIG. 7 shows schematically an active form of an enzyme and an inactive form of the enzyme having common epitopes.

The above dichotomy has been demonstrated experimentally; the antibodies produced following the tolerising regime are more specific than those produced using a normal immunisation procedure, but they are of lower affinity. To overcome this, it is proposed to administer whole IgG as the tolerogen, then give anti-IgG Fc at the time of immunisation with free lambda (see FIG. 6). This will inhibit all B cells recognising exposed lambda epitopes, so that only B cells recognising hidden lambda epitopes will be stimulated. Thus, only antibodies recognising hidden lambda epitopes will be produced. Experimental results consistent with this have been achieved.

EXAMPLE 3

Producing Specific Antibodies to the Active Form of an Enzyme

This follows the same basic principle used in Example 2. In this case it is desired to produce antibodies that react only with the active form 70 of an enzyme, and not with any of the common epitopes 71, 72, that are present on both the active (70) and inactive (73) forms.

Figure 8:
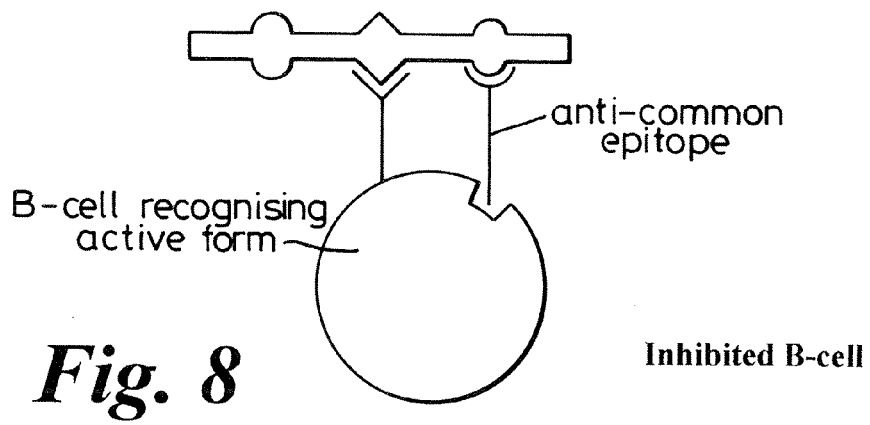
FIG. 8 shows a B-cell which would produce antibodies specific to the epitope exclusive to the active form of the enzyme if it were not inhibited by antibodies to a common epitope binding to the common epitope and the $F_c$ receptor.

One initial approach could be to raise antibodies to the inactive enzyme 73, and use these to tolerise. However, when immunising with the active form of the enzyme, B cells recognising the active form epitopes 74 are likely to be inhibited in an analogous situation to that shown in FIG. 5 (see FIG. 8).

Figure 9:
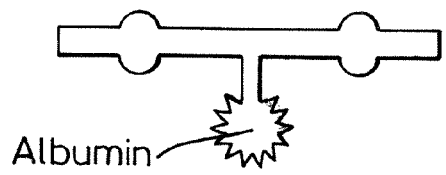
FIG. 9 shows a modified form of the enzyme, having albumin coupled to it.
Figure 10:
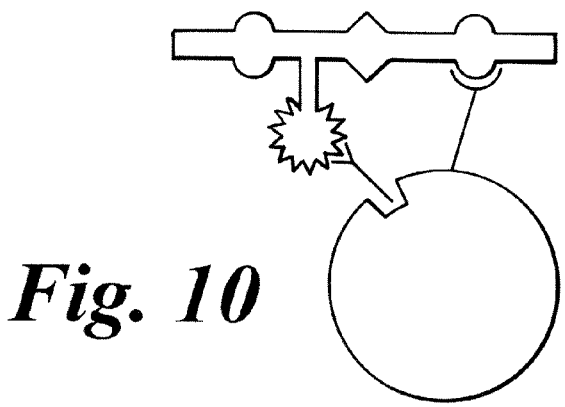
FIG. 10 shows the inhibition of B-cells which recognise common epitopes by administering anti-albumin.

This problem can be overcome by conjugating a suitable carrier protein (e.g. albumin) to the inactive enzyme (see FIG. 9) and then administering this as a tolerogen. The active enzyme would then by given as the immunogen, together with anti-albumin. This would result in inhibition of B cells recognising common epitopes—see FIG. 10. Thus, only B cells recognising active form epitopes 74 would be stimulated, resulting in active form specific antibodies being produced.
Producing Specific Antibodies—Examples

Having now described the three general areas in which we see the present invention having applications, and having discussed a theory which we believe explains the present invention, we shall now describe specific examples in relation to each, by way of example only, with reference to FIGS. 11a to 17:—

Figure 11A:
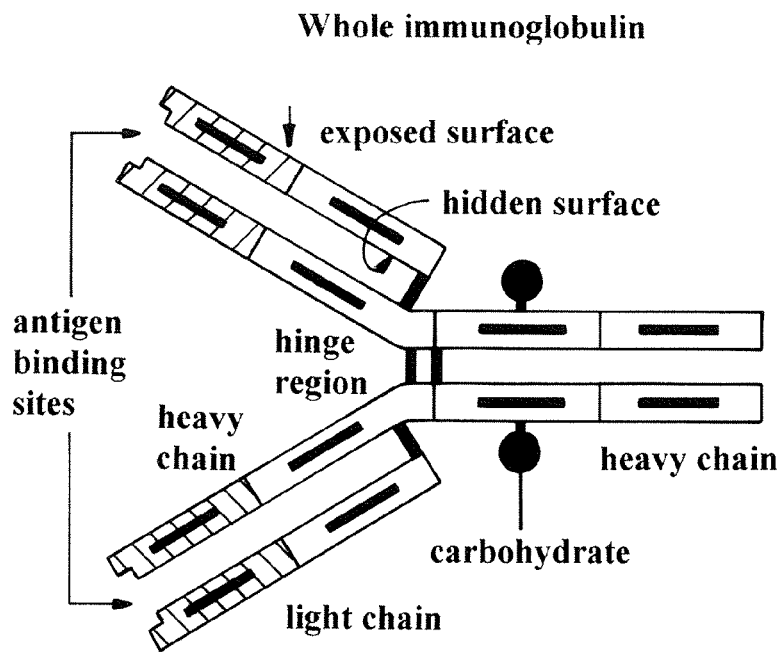
FIG. 11a shows a paraprotein having light chains bound to its heavy chains.
Figure 11B:
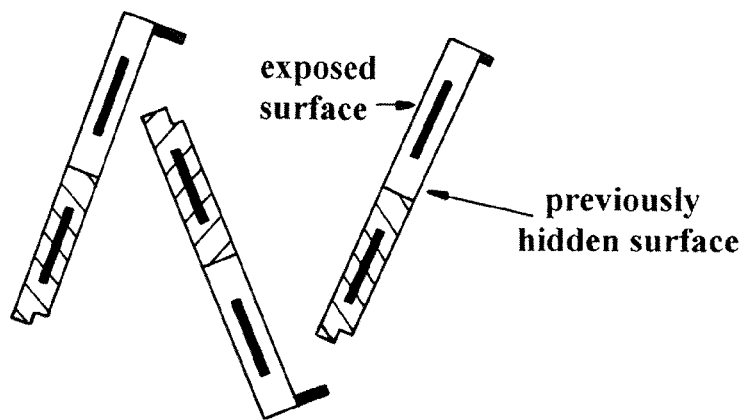
FIG. 11b shows the light chains of FIG. 1a with its hidden determinants exposed.

Multiple myloma can be detected by looking for paraproteins in the urine of patients. In normal people tiny amounts of paraprotein are present in the blood. FIG. 11a shows schematically a paraprotein. If plasma cells (bone cells) are de-differentiated they can produce a part of the paraprotein, the light chains. These are much smaller than the whole paraprotein (25 kD cf. 150 kD) and are excreted into urine by the kidneys. FIG. 11b schematically shows the lambda light chains of the paraprotein of FIG. 11a. Thus a multiple myloma can be detected by noticing high levels of kappa and/or lambda light chains of the plasma cells. At present the presence of the light chains is detected using antibody binding and electophoretic techniques. The antibodies used react with free light chains, and also with light chains bound to heavy chains. This can mean that the test can show a positive result for whole paraproteins, which might be present for a variety of reasons not necessarily associated with myloma (e.g. kidney damage can allow the whole paraproteins to pass through).

In this example the present invention comprises producing antibodies that are specific to the hidden determinants of the light chains (which will not be available for binding in the whole paraprotein, only when there are free light chains).

The production of such specific antibodies can be enhanced by tolerising the host antibody-producing animal with antibodies to the remainder of the paraprotein—the exposed determinants (i.e. tolerise with paraprotein with bound light chains), and immunising the animal with free light chains of the paraprotein. This causes in the host animal those B-cells that recognise the exposed determinants to be switched off, leaving only B-cells recognising the hidden determinants; thus only antibodies to the hidden determinants are produced.

These hidden determinant specific antibodies are then extracted from the host animal and used in the production of kits for immunological assays. The kits can be used to detect the free light chains in urine, or even in blood.

The process enables the production of high affinity polyclonal antisera to free kappa and lambda light chains. These antisera find uses in tests and test kits.

What it is proposed to do in practice is in one example to immunise one animal (e.g. a sheep, sheep A) with a non-selected part of a protein. The antibody to the non-selected protein would then be extracted from the animal's blood (eg a pint of blood would be taken, with the sheep still in good health) and purified with an affinity purification technique.

Another sheep, sheep B, that had not been immunised with the whole protein, nor with the non-selected part of the protein, would be taken and injected with the antibodies from sheep A that react only with the unwanted, non-selected, part and also, at the same time, the antigen that is whole of the protein that the selected part forms a part of (in the case of paraprotein with the free light chains).

Antibodies from the blood of sheep B would then be extracted (eg 100 ml to 1 liter of blood taken, leaving the sheep in good health), and these would be antibodies which were specific to the selected part of the protein. They would be used in a kit. Alternatively they might first be purified and then used in a diagnostic kit.

It will be appreciated that instead of injecting the whole of the protein that the selected part forms part of it is possible to consider injecting just the selected part, but that would be more expensive to make, and may not even be possible.

It will be appreciated that one main use of antibodies made in accordance with the present invention is in an immuno assay for measuring free immunoglobulin light chains, preferably in automated test apparatus. The example discussed in relation to FIGS. 11a and 11b was to look for multiple myeloma, but the technique is also, of course, suitable for testing for other paraproteinaemias.

In addition to performing a test to detect whether a patient has a paraproteinaema tests would also be performed to monitor the patient periodically.

It is a known technique to attach antibodies to particles in order to improve the sensitivity of a test. It is possible that the antibodies produced would be linked to a particle (e.g. a polystyrene microsphere). This may be another stage in the production of test antisera.

It will be appreciated that in the example of FIGS. 11a and 11b a specific antibody to a single part of a molecule, and not to other parts of the molecule (or to the difference between two similar molecules) is produced.

This invention has wide application. For example, applying the same concept to an enzyme allows the production of an antibody specific to the active site of the enzyme (e.g. by tolerising with the enzyme in inactivated state, and immunising with the enzyme in activated configuration).

As discussed in relation to FIGS. 7 to 10 it is possible to immunise to produce antibodies specific to the difference between two states of a molecule. It is possible to produce antibodies only to the active form of an enzyme, or molecule, and not the inactive form (or substantially only to the one form). This can be used to produce a functional assay (one that looks at whether a particular enzyme is functional). In this case the "selected part" of the molecule could be the active site in its active configuration, and the non-selected part could be the entire inactive molecule.

One particular area where the invention may have a commercial use is in the production of catalytic antibodies. It is known that antibodies can act as catalysts in chemical reactions: just as enzymes catalyse reactions some antibodies can also catalyse a specific reaction. It is believed that catalytic antibodies bind one or more of the reaction molecules at a "pocket" or binding site and force it to have the right shape/charge distribution to undergo the chemical reaction that the antibody catalysises. In the production of a catalytic antibody a template antigen of an appropriate shape/size and charge is used to produce an antibody to it. The present invention allows catalytic antibodies to be produced better by, for example, tolerising with antibodies to non-template antigen (or with the non-template antigen itself) and then immunising with the template antigen. It is preferred to tolerise with antibodies to the non-template antigen (or antigens) since it is believed that this gives better antibodies to the template antigen.

Of course, a catalytic antibody produced using the present invention need not be used in a blood or urine test kit. It may be used in vivo to catalyse its reaction in order to obtain the reaction products (or destroy the reaction starting materials). Alternatively it could be used in vitro to catalyse the reaction in question. Indeed, this might be one way of helping some people or animals that have a defective enzyme in their metabolism. One aspect of the invention may be thought of as the use of antibodies X, in the preparation of a medicament Y, for the treatment of a condition Z; where Z is related to a defective enzyme, and the antibody X catalyses the reaction of the defective enzyme, and the antibody X has been made in accordance with any other aspect of the invention.

The idea of using antibodies X in the preparation of a medicament Y for the treatment of condition Z is not restricted to enzyme-related conditions, but is applicable to any condition associated with the presence or absence of a physiologically active substance.

The idea of using tolerisation/immunising to produce an enhanced response to a specific part, or epitope, is a tool to exploiting the activity of that part, or epitope, and/or antibody.

It has been appreciated that if the B cells to a part of a molecule are switched off it is possible to get a good antibody response to the other part of the molecule. Limiting the response to specific molecules in an antigen mixture by administering antibodies to the undesired antigens at the time of immunisation is how it is preferred to produce the desired antibodies.

Returning to the example of FIGS. 1a and 1b this is the first time that it has been possible to produce polyclonal antisera against hidden epitopes on single molecules.

In addition to using the invention to produce antibodies to a part only of a molecule it can be used to produce antibodies to one molecule, but not another similar, but different molecule (different allotypes). This enables us to provide a sensitive probe to different allotypes.

It will be appreciated that the method of diagnosis will not normally be practised on a human or animal body, but rather on a sample (e.g. blood, urine, tissue) extracted from the body.

It will be appreciated that the present invention allows the production of antibodies faster, and to only a part of a molecule, and enables a greater concentration in the animal extract of antibodies of the desired kind to be obtained.

The selected part of the molecule (for which antibodies are not required) may be substantially all of the molecule except the non-selected (or de-selected) part. If the non-selected part of the molecule is the part that gives it its physiological effect we can make antibodies to all of the molecule except the physiologically active part. This is very convenient from the point of view of providing a range of antibodies to tolerise a patient to allow repeated administrations of the molecule.

Specific Switching Off of a Patients Immune Response to Specific Antigens for Beneficial Effect An example of the invention as it relates to the switching off of selected immune responses for medical reasons will now be given, by way of example only, with reference to the further figures of the drawings.

We have already provided an initial discussion of a mechanism we believe operates, but we will now apply it to the example of using Botulinus Toxin to treat muscle spasms.

Figure 12:
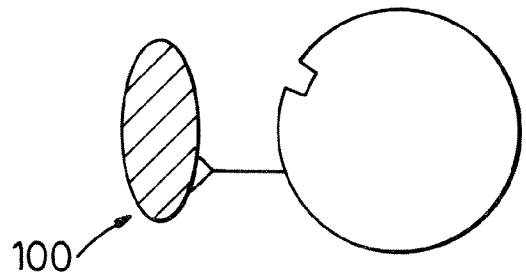
FIG. 12 shows a naive B cell with Botulinus toxin bound to a receptor.

A naive B cell that has not previously been exposed to the protein structure of a Botulinus Toxin, will when a Botulinus toxin antigen binds to a receptor on the B cell, produce a primary antibody response (see FIG. 12). In due course (over several days) memory cells will be produced. These can produce antibodies to the Botulinus toxin antigen very quickly (in hours), and in vast numbers.

Figure 13:
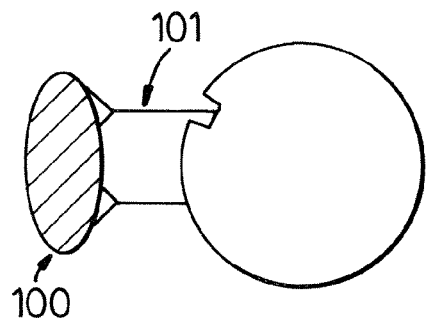
FIG. 13 shows the naive B cell of FIG. 12 with the response inhibited by the presence of anti-botulinus toxin antibody bound to its Fc receptor.
Figure 14:
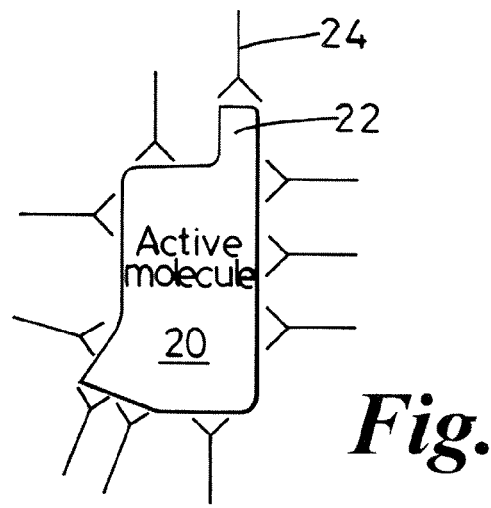
FIG. 14 shows a Botulinus Toxin with different antibodies bound to different regions or parts of its structure.

FIG. 13 shows the B cell of FIG. 12, but with an antibody 101 to the antigen 100 bound to the Fc site. This effectively switches off the B cell, preventing the production of primary antibodies, and preventing the development of memory B cells.

When an antibody touches the Fc receptor it switches off the naive B cell for some time, even after the antibody has disassociated from the B cell. The B cell may be switched off for about a day. Whilst it is switched off it produces no substantial, immunological response consequential to the presence of the antigen 100.

The heart of our invention is that this known mechanism is not merely a curiosity, but can be used for substantial beneficial effect to switch off the immune response to particular, specific, antigens by ensuring that there are antibodies present to the chosen antigens to prevent the activation of naive B cells.

We do not want to switch off the entire immune system since that will do more harm than good, but switching off the response to narrow antigens only (or a single antigen) will allow us to administer those antigens.

A particular molecule e.g. Botulinus Toxin, will elicit a number of antibodies specific to different protein regions that it has. The Botulinus molecule 20 of FIG. 14 has a physiologically active part, 22, which enables it to perform the desired physiological effect when injected into patients to relieve muscle spasm.

A particular antibody, antibody 24, produced by the immune system binds to active part 22.

If the antibody 24 binds to active part 22 with too high an affinity (too tightly/remains associated with it for too long and does not disassociate for long enough) it can interfere with the physiological effect of the active part of molecule 20. If we were to tolerise a patient to all of the parts of the whole molecule 20 with too high a dose of antibody there is a chance that the antibodies 24 would prevent/hinder the proper effect of the molecule 20 from taking place, making the administration of the antigen 20 pointless.

Thus we have appreciated that we must either: a) have the antibodies present at a low enough level so that the active site remains active; or b) not introduce (tolerise with) antibodies to the active part 22 so as to leave it operational; or c) have the antibodies 24 that are directed against the (or an) active region of low enough affinity that the active part is "exposed"/free of interference for long enough (or for a long enough fraction of the time) for it to have the desired physiological effect.

If we do not tolerise to the active part 22 at all there is a risk that the Immune System of the patient will produce antibodies to part 22, since naive B cells are not switched off to part 22, and a primary/response to part 22 may develop. However, the part 22 can elicit a much smaller response than the whole molecule, giving an overall benefit in tolerising to just part of the molecule (the molecule stays in the blood/body tissues for longer because there are fewer regions where available antibodies bind to it, and less cross-linking).

Furthermore, if there is a primary immune response to part 22 there will in due course (if the antigen remains in the blood/body) be a secondary response with memory B cells, but again the overall effect will be less than if the whole of the molecule elicited a response. If antibodies only to part 22 bind to the molecule it may be more difficult for them to cross-link (in comparison with lots of different antibodies binding to different sites) and so the molecule may stay available to the body for longer.

If a second or third introduction of molecule 20 is given over a period of months then a secondary immune response to part 22 may occur. Ideally, we would prefer to switch off the immune system to the active part of the molecule without destroying its physiological activity. This may be achieved by using a suitably low dose of antibodies when tolerising.

We may ensure that we tolerise with low affinity antibodies to the active part of the molecule to try to achieve this effect.

We may tolerise with low affinity antibodies to the non-active parts of the molecule, or with high affinity antibodies.

The level of antibodies that we give to tolerise is, as will be appreciated, very low. We might inject 1, 2, 3, 4, 5, 6, 7, 8, 9, 10 or more microgrammes of antibody. We do not need to inject much, just enough to switch off the B cells (or many of them). This level of antibodies is too low to have any significant risk of an adverse reaction from a patient.

A key part of the present invention is the realisation that we do not simply have to accept that the immune system of a patient will render repeat treatments ineffective. A further surprising step is the realisation that contrary to first thought, it is not counterproductive to tolerise to a molecule because this will block its physiological effect: we can still have a physiological effect (and a reduced/eliminated immunological response) either by having a low enough dose of antibody, by tolerising to part only of the molecule, or by ensuring that there is a low affinity antibody to the active part (allowing it to be active for a significant time).

The immunological mechanisms of which we take advantage are not new, nor are they newly understood: it is the realisation that they can be used to augment/complement a treatment that is at least a part of our invention.

At present patients with muscle spasm (e.g. of the neck or face muscles), are treated by injecting a Botulinus Toxin (e.g. DUSPORT™ produced by Speywood Pharmaceuticals Ltd, SL6 4UH); or BOTOX produced by Allergan Ltd, HP12 3SH, both UK companies).

Injections of the Botulinus Toxin are given intramuscularly (in the case of an eye muscle spasm there is little difference between intramuscular injection and subcutaneous injection because the muscles are so small). In a significant number of patients their response falls off after a number of injections.

In the present invention we inject the recommended dose of Botulinus Toxin and also a dose of antibodies, the dose of antibodies being in the microgram range. The antibodies would be antibodies to all (or substantially all) of the Botulinus Toxin, but at a low dose (eg 25 µg or above).

There would be little or no immune response, and the reduction of response of the patient to Botulinus injections beyond a minimal level would ideally never happen, or be delayed by a significant number of injections. In a significant number of patients we would expect never to see a reduction in response to a level where it was not worth further injections.

Figure 15:
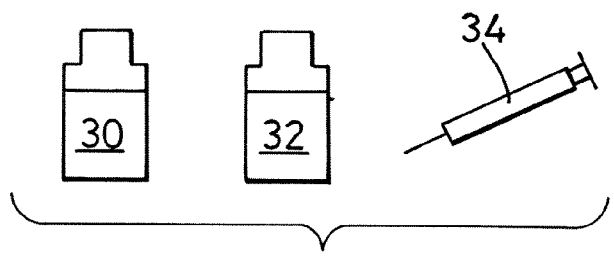
FIG. 15 shows a bottle of Botulinus Toxin and a bottle of antibodies, and a syringe.

We may inject the antibodies simultaneously with the Toxin, or shortly before or after. Referring to FIG. 15, a few micrograms of antibodies 32 are introduced into the syringe 34 either immediately before or after the volume of Toxin is introduced, and the two injected simultaneously from the same syringe. Alternatively we may have two syringes—one for the antibodies and one for the Botulinus Toxin. We may provide pre-loaded syringes for the antibodies.

We may use a multi-component injector that mixes the medicament constituents as they are injected. The or each component of the medicament may be provided as a cartridge/sample of predetermined volume.

After a first injection with both antibodies and Botulinus Toxin a patient may receive subsequent injections of just Toxin whilst his immune system is still switched off. Alternatively we may give further antibodies to the Toxin (or to the non-active part of the Toxin) with each (or at least some) subsequent administrations of the Toxin.

It will be appreciated that if our suggested mechanism is correct the invention is best performed on patients who have not previously been injected with. Botulinus, and which therefore have naive B cells to the Toxin.

The ability to keep on giving injections of the Botulinus Toxin removes the need to, and cost of, developing an alternative strain of Botulinus.

For a second example, take the first example relating to Botulinus Toxin and replace it with Streptokinase for treating heart attacks.

There is, of course, the practical steps for the user of being able to produce antibodies to part only of the antigen molecule in question. This is covered in the earlier part of this patent application.

It will be appreciated when we want to make an antibody specific to a selected part of a molecule we can tolerise to the immunological antibodies to a non-selected part of a first molecule by introducing antibodies to the non-selected fragment of the first molecule in question, or by introducing antibodies to another molecule, a second molecule, that has the non-selected part of the first molecule in question plus another part or parts (but not the selected part of the first molecule). The antibodies to the non-selected part and/or to the selected part are preferably extracted from an animal in a way which still leaves the animal alive, possibly for further harvesting of antibodies. For example, an animal could be bled and the antibodies extracted from its blood. It is quite possible to take 100 ml to 1 liter of blood from many animals without doing them permanent harm, and leave the animal available for further antibody harvests in the future. The antibody source that is used to produce the antibody to the non-selected part is preferably not the same source (animal) that is later used to produce the antibody to the selected part. That is to say a different source (animal of the same species) has the antibody to the non-selected part used to tolerise it for the production of antibody to the selected part.

Areas where the present invention has applications include, in a non-exhaustive list:—

Interferons are used to treat multiple sclerosis may cause an immune response.

Botulinus toxins for treating muscle spasms may elicit an immune response. There may be other neurological applications.

Substances for the treatment of rheumatic disease may cause there to be a detrimental immune response. For example TNF, selections, and other cytokines.

The treatment of tumours with substances. Antibodies, e.g. monoclonal antibodies, can be used for tumour targeting in diagnosis or therapy. Antibodies to a part of a tumour structure, e.g. epitope, or more than one epitope, can be made and bind, in use, to those epitopes. Other things can be attracted to/bound to/complex with the antibodies, such as drugs to treat the tumour, or something that is easily detected by a scanner such as a NMR scanner, or a CAT scanner, or an X-ray machine.

We aim, of course, to switch off a patients immune response to foreign "targeting" antibodies that are introduced to target a structure (e.g. a tumour). For example use may tolerise to the whole of, or to the majority of, their structure. We may choose not to tolerise to their active binding site that locks onto their target. Tolerising the immune system of the patient to the targeting antibodies allows them to be more effective since they are not so strongly removed by the immune system of the patient.

Substances for use in cardiology offer another use for the present invention. Streptokinase is used to treat myocardial infarction, and the patients immune system prevents the administration of a second dose. The present invention may allow a second and further dose to be given.

The reduction of immune response (IgE) to pharmaceutical antisera, such as botulism and diphtheria antitoxins offers another area of use. Reducing the response to antitoxins can enable them to perform better/last longer in the body. Antitoxins to treat snake bite venom, or other venoms, is another area of use.

Haematology offers a wide area of use. Injecting patients with foreign proteins, e.g. Factor VIII to treat haemophiliacs, is well known. The present invention allows us to reduce or substantially eliminate the patients immune response to the foreign Factor VIII (or other substance).

It is also known to use antibodies for therapeutic use, e.g. the removal of toxic drugs (Fab antibodies are injected into people suffering from digitalis poisoning). The present invention allows us to "hide" the injection antibodies from the immune system of the patient by tolerising to their foreign structure/protein, whilst allowing their active, toxin-interacting region still to function.

Monoclonal antibodies are used in control organ rejection, following transplant surgery. Switching off the immune response, selectively, to the antibodies that are administered for that purpose is another use of the invention. We can tolerise at a low dosage with the anti-rejection antibodies and thereby minimise the immune system response to them, allowing them to act better and for longer.

We may even see a use for the invention in tolerising the immune system of a patient to specific antigens of a transplanted organ, preventing/delaying its rejection. The transplanted organ can be considered to be the foreign "administered" substance (within the meaning of the claims).

A further area of use is treatment with erythropoetin to help alleviate kidney problems. This elicits an immune response, which can be modified using the present invention.

A further area of use is that we can now give an injection of an antigen, antigen A, that is not pure antigen A and switch off the immune response to the impurities by tolerising the immune system with antibodies, at a suitably low dose, to them, leaving a response substantially only to the antigen A. This enables us to use a cheaper, less pure, antigen A. Much of the costs of many drugs or vaccines is associated with purifying them. We may be able to reduce the purification costs in this way (eliminating the need for such pure substances).

Indeed, any area where a complex protein/antigen that includes an immune response (that is unwanted) is an area where this invention can be used.

The antibodies that we introduce preferably have a high affinity for the proteins they attach to. We may prefer to have low affinity antibodies, if there are any antibodies at all, to the active site (S).

We prefer to inject the physiologically active substance and the antibodies to it at about the same site on the human or animal (possibly sequentially, or simultaneously). We may prefer to inject the substance at one site and the antibodies at another. The two sites may be well spaced apart. One or both of the sites may be subcutaneous, intravasular, or intramuscular.

Suppressing Immune Response to Foreign Substance by Associating the Substance with an Antigen and Ensuring that Antibodies to that Antigen are Present (eg Selecting an Antigen to which there is a Pre-Existing Population of Antibodies in the Body).

As an example of the industrial application of this invention we shall take the administration of stroptokinase to patients suffering from myocardial infarction. The example will be described by way of example only, with reference to the accompanying FIGS. 16 and 17 which accompany this application.

In order to prevent the production of antibodies to streptokinase in a patient upon the first administration of streptokinase to that patient (or upon subsequent administrations), one could covalently attach another molecule to it (eg albumin). This conjugate could then be administered together with anti-albumin, and any B cells recognising streptokinase would be "switched off". Thus no antibodies to streptokinase would be produced—see FIG. 16.

A disadvantage of this is that the antibodies to albumin would have to be human antibodies, in order to bind to the human Fc receptor of the patients B cells. Such human antibodies are not readily obtainable.

An alternative would be to replace albumin as the conjugated molecule with Rhesus D antigen; human antibodies to Rhesus D are commercially available. Administering anti-Rhesus D could not be undertaken with Rhesus-positive patients however, since the antibody would bind to the Rhesus D antigen on the patients' red cells.

A better option would be to replace albumin with a molecule such as tetanus toxoid. Many individuals are routinely immunised with tetanus toxoid as protection against tetanus; they therefore already have antibodies present to this in their circulation. (If anti-tetanus toxoid levels are too low or are absent, the patient can be immunised/boosted with tetanus toxoid which may be given at the same time as the streptokinase-tetanus toxoid conjugate). If the streptokinase-tetanus toxoid conjugate is administered, the anti-tetanus toxoid antibodies already present will prevent production of antibodies to streptokinase (see FIG. 17). There is thus no need to administer any antibodies. The advantages of this approach are as follows:

i. Unconjugated streptokinase can be given at the same time as the streptokinase conjugate. This means that any loss of streptokinase's enzymic activity that might result from the conjugation process would be compensated for. The B cells that recognise streptokinase would still be switched off by the conjugate, or the vast majority of them.

ii. No antibodies need to be administered to the patient.

iii. This is a "single shot" treatment. (An initial screen of the patient's immunity to tetanus toxoid may be necessary or desirable, however).

This procedure could be applied to any medical situation where a substance has to be given on more that one occasion and it is essential that antibodies to that substance are not produced.

With hindsight, after making the invention, it can be seen that the process is analogous to the situation that occurs naturally when (naive) B cells are exposed to different variants of influenza virus. Here a first virus strain creates B cells responsive to its epitopes, and when a second virus strain is encountered the epitopes common to both strains generate a larger response than that generated with the first contact with the original strain, but the new epitopes on the second virus, not seen before, generate a much weaker response than they would have had the second strain encountered an immune system that had not already encountered the first strain.

We would propose administering a physiologically (or pharmacologically) active substance conjugated with an antigen to which a patient already had an existing antibody population. We may also administer unconjugated physiologically/pharmacologically active substance at the same time. "At the same time" does not necessarily mean in the same injection, or within seconds of the conjugated injection—it may be hours, or even a day, or more, after. We would not envisage administering unconjugated active substance too long before administering the B cell switch-off conjugate.

We envisage providing a kit of one or more of:—a container with conjugate; instructions; an injector; unconjugated active substance (either in with the conjugated substance or in a separate container; a test kit to determine the presence of a desired existing antibody population.

Instead of conjugating/binding to tetanus toxoid another antigen to which there is a pre-existing antibody population may be used. For example many people in some countries have inoculations against a variety of diseases. "Dead" antigen for such diseases could be used. In the UK and other countries the human population is widely inoculated against many diseases, and widely experiences many "childhood" diseases. Chicken pox, tuberculosis, mumps, whooping cough, typhoid, polio, scarlet fever, and many other antigens will have a large part of the human population having antibodies to them.

The kit that we provide may contain a number of different antigen-physiologically active substance conjugates with different antigens, the user selecting the desired antigen/active substance conjugate after performing a screening test that looks for a number of antibodies (corresponding to the available antigen conjugates).

What I claim is:

1. A method of producing antibodies that are specific to hidden epitopes of immunoglobulin light chains, said hidden epitopes being epitopes that are hidden when a light chain is bound to a heavy chain and which are not available for binding to antibodies in a whole immunoglobulin, the method comprising:

making antibodies to a selected part P of an immunoglobulin molecule ZP, a Z molecule comprising the non-selected part of the molecule ZP, P being the selected part of the molecule ZP which comprises a hidden epitope of the light chain, wherein said method comprises tolerising the immune system of a source of antibodies to the Z molecule or a part of the Z molecule that hides the selected part P, by administering to the antibody source a compound containing the non-selected part Z or a part of non-selected part Z of the molecule ZP and also administering to the antibody source antibodies to the non-selected part Z or part of Z of the immunoglobulin molecule ZP; wherein these administered antibodies are specific to an Fc region of the immunoglobulin molecule ZP;

and immunising the source of antibodies with part of ZP having the selected part P exposed, and allowing the source of antibodies to produce antibodies to said selected part P of the immunoglobulin molecule ZP; and wherein said non-selected part Z comprises non-hidden epitopes of said immunoglobulin molecule, and wherein said compound containing the non-selected part of said molecule comprises a whole immunoglobulin, and wherein immunising the source of antibodies with part of ZP comprises immunising with free light chain.

2. A method of producing antibodies that are specific to hidden epitopes of immunoglobulin light chains, hidden epitopes being epitopes that are hidden when a light chain is bound to a heavy chain and which are not available for binding to antibodies in an intact immunoglobulin, the method comprising administering to an animal source of antibodies having an immune system intact IgG as a tolerogen and also administering to the animal antibodies specific to IgG Fc, wherein the antibodies specific to IgG Fc and the intact IgG are administered simultaneously or sequentially, and also immunising with free light chain, wherein the free light chain is administered simultaneously or sequentially with intact IgG tolerogen and antibodies to IgG Fc.

3. A method according to claim 2 wherein said anti IgG Fc antibodies are administered to the animal at the time of immunisation of the animal with free light chain.

4. A method of producing antibodies that are specific to hidden epitopes of immunoglobulin light chains, said hidden epitopes being epitopes that are hidden when a light chain is bound to a heavy chain and which are not available for binding to antibodies in an intact immunoglobulin, the method comprising administering to animal intact IgG as a tolerogen and then administering to the animal antibodies specific to IgG Fc at the time of immunising the animal with free light chain.

5. A method of producing antibodies that are specific to hidden epitopes of immunoglobulin light chains, said hidden epitopes being epitopes that are hidden when a light chain is bound to a heavy chain and which are not available for binding to antibodies in an intact immunoglobulin, the method comprising administering to an animal intact IgG as a tolerogen and then administering to the animal antibodies specific to IgG Fc at the time of immunizing the animal with free light chain, and wherein the method further comprises using an animal which is naïve to the intact IgG administered as a tolerogen.

6. A method of producing antibodies that are specific to hidden determinants of immunoglobulin light chains, said hidden determinants being epitopes that are hidden when a light chain is bound to a heavy chain and which are not available for binding to antibodies in an intact immunoglobulin, the method comprising tolerising an antibody producing animal with immunoglobulin paraprotein having bound light chains and with antibodies to exposed determinants of the immunoglobulin paraprotein with bound light chains, with hidden determinants of the bound light chains not being available for binding to antibodies of the animal and immunizing the animal with free light chains of the immunoglobulin paraprotein, wherein the antibodies to exposed determinants of the immunoglobulin paraprotein with bound light chains are specific to an Fc region of the immunoglobulin.

7. The method of claim 6 comprising extracting antibodies to the hidden determinants from the animal's blood.

8. The method of claim 7 further comprising purifying the antibodies to the hidden determinants using an affinity purification technique.

9. A method of producing antibodies that are specific to hidden epitopes of immunoglobulin light chains, said hidden epitopes being epitopes that are hidden when a light chain is bound to a heavy chain and which are not available for binding to antibodies in an intact immunoglobulin, the method comprising, injecting an animal, as a source of antibodies, with free light chain, tolerizing with intact immunoglobulin and antibodies that bind only to parts of immunoglobulin that are not the hidden epitopes and that do not bind to said hidden epitopes of said light chains, wherein the antibodies that bind only to parts of immunoglobulin that are not the hidden epitopes and that do not bind to said hidden epitopes of said light chains are specific to an Fc region of the immunoglobulin.

10. A method according to claim 9 further comprising producing said antibodies that bind only to parts of immunoglobulin that are not the hidden epitopes by immunizing a different animal to said source of antibodies animal, but of the same species, with intact immunoglobulin with light chain bound to heavy chain.

11. A method of making antibodies specific for epitopes on free immunoglobulin light chains which are hidden and will not be available for binding in an intact immunoglobulin but are exposed on free immunoglobulin light chains comprising tolerising the immune system of a first non-human animal source of antibodies with immunoglobulin with bound immunoglobulin light chain and with antibodies to exposed epitopes of the immunoglobulin, wherein the antibodies to exposed epitopes of the immunoglobulin are specific to an Fc region of the immunoglobulin;

and immunizing the first source of antibodies with free immunoglobulin light chain and allowing the first source of antibodies to produce antibodies specific for the free immunoglobulin light chain, and extracting said antibodies to the hidden epitopes produced from the first source, and in which a second source of antibodies is used to produce the antibodies to the exposed epitopes of the immunoglobulin which second source is not the same individual non-human animal source as the first source that is later used to produce the antibody to the hidden epitopes on the free immunoglobulin light chains, and in which the first source chosen to produce the antibody to the free immunoglobulin light chain has not been immunized with the immunoglobulin beforehand.

12. A method of making antibodies specific for determinants on free immunoglobulin light chains which are hidden and will not be available for binding in an intact immunoglobulin but are exposed on free immunoglobulin light chains, comprising tolerising an antibody-producing non-human animal with intact immunoglobulin with bound light chains and antibodies to the exposed determinants on the intact immunoglobulin, wherein the antibodies to the exposed determinants on the intact immunoglobulin are specific to an Fc region of the intact immunoglobulin;

and immunizing the animal with free immunoglobulin light chains of the immunoglobulin, and allowing the animal to produce antibodies to the hidden determinant exposed on the free immunoglobulin light chain, and extracting antibodies from the animal specific for the hidden determinants exposed on the free immunoglobulin light chains.

13. The method of claim 8 wherein tolerising comprises injecting said intact immunoglobulin intravenously.

14. The method of claim 13 wherein the immunoglobulin is injected intravenously and in the absence of adjuvant.

15. The method of claim 6 wherein tolerising with immunoglobulin having bound light chains is performed as a separate step to immunizing with free light chain.

16. The method of claim 11, wherein the free light chains are kappa light chains.

17. The method of claim 11, wherein the free light chains are lambda light chains.

18. The method of claim 12, wherein the free light chains are kappa light chains.

19. The method of claim 12, wherein the free light chains are lambda light chains.

20. A method of producing antibodies that are specific to hidden epitopes of immunoglobulin light chains, said hidden epitopes being epitopes that are hidden when a light chain is bound to a heavy chain and which are not available for binding to antibodies in a whole immunoglobulin, the method consisting of:

making antibodies to a selected part P of an immunoglobulin molecule ZP, a Z molecule comprising the non-selected part of the molecule ZP, P being the selected part of the molecule ZP which comprises a hidden epitope of the light chain, wherein said method consists of tolerising the immune system of a source of antibodies to the Z molecule or a part of the Z molecule that hides the selected part P, by administering to the antibody source a compound containing the non-selected part Z or a part of non-selected part Z of the molecule ZP and also administering to the antibody source antibodies to the non-selected part Z or part of Z of the immunoglobulin molecule ZP; wherein these administered antibodies are specific to an Fc region of the immunoglobulin molecule ZP;

and immunising the source of antibodies with part of ZP having the selected part P exposed, and allowing the source of antibodies to produce antibodies to said selected part P of the immunoglobulin molecule ZP; and wherein said non-selected part Z comprises non-hidden epitopes of said immunoglobulin molecule, and wherein said compound containing the non-selected part of said molecule comprises a whole immunoglobulin, and wherein immunising the source of antibodies with part of ZP comprises immunising with free light chain.

21. The method of claim 1, wherein the tolerising of the antibody source is performed prior to the immunizing of the antibody source.

22. The method of claim 20, wherein the tolerising of the antibody source is performed prior to the immunizing of the antibody source.

23. The method of claim 1, wherein the tolerising step is performed by intravenous administration of the compound containing the non-selected part Z or the part of the non-selected part Z of the molecule ZP, and the antibodies to the non-selected part Z or the part of Z of the immunoglobulin molecule ZP.

24. The method of claim 2, wherein the antibodies specific to IgG Fc and the intact IgG are administered intravenously.

25. The method of claim 4, wherein the intact IgG and the antibodies specific to IgG Fc are administered intravenously.

26. The method of claim 5, wherein the intact IgG and the antibodies specific to IgG Fc are administered intravenously.

27. The method of claim 6, wherein the tolerising step is performed intravenously.

28. The method of claim 9, wherein the tolerising step is performed intravenously.

29. The method of claim 11, wherein the tolerising step is performed by intravenous administration of the immunoglobulin and the antibodies to the exposed epitopes of the immunoglobulin.

30. The method of claim 12, wherein the tolerising step is performed by intravenous administration of the intact immunoglobulin and the antibodies to the exposed determinants of the intact immunoglobulin.

31. The method of claim 20, wherein tolerising is performed by intravenous administration of the non-selected part Z or the part of the non-selected part Z of the molecule ZP, and the antibodies to the non-selected part Z or the part of Z of the immunoglobulin molecule ZP.

* * * * *